(12) United States Patent
Lell

(10) Patent No.: US 7,160,265 B2
(45) Date of Patent: Jan. 9, 2007

(54) NEEDLELESS INJECTION DEVICE WITH PYROTECHNIC DRIVE

(75) Inventor: Peter Lell, Am Mullbachbogen 85, Moosburg D-85368 (DE)

(73) Assignee: Peter Lell, Moosburg (DE)

( * ) Notice: Subject to any disclaimer, the term of this patent is extended or adjusted under 35 U.S.C. 154(b) by 588 days.

(21) Appl. No.: 10/311,200

(22) PCT Filed: Jun. 20, 2001

(86) PCT No.: PCT/DE01/02271

§ 371 (c)(1),
(2), (4) Date: Dec. 13, 2002

(87) PCT Pub. No.: WO01/97880

PCT Pub. Date: Dec. 27, 2001

(65) Prior Publication Data

US 2004/0049151 A1    Mar. 11, 2004

(30) Foreign Application Priority Data

Jun. 20, 2000   (DE) ................. 100 29 325

(51) Int. Cl.
*A61M 5/30* (2006.01)
(52) U.S. Cl. .......................... 604/69; 604/72
(58) Field of Classification Search .......... 604/65, 604/66, 67, 68, 69–72, 140, 141; 128/DIG. 12
See application file for complete search history.

(56) References Cited

U.S. PATENT DOCUMENTS

| 3,308,818 A | | 3/1967 | Rutkowski | |
| 4,089,334 A | * | 5/1978 | Schwebel et al. | 604/69 |
| 5,080,648 A | * | 1/1992 | D'Antonio | 604/72 |
| 5,399,163 A | * | 3/1995 | Peterson et al. | 604/68 |
| 5,499,972 A | * | 3/1996 | Parsons | 604/68 |
| 5,503,627 A | * | 4/1996 | McKinnon et al. | 604/72 |
| 5,503,628 A | | 4/1996 | Fetters et al. | |
| 5,836,911 A | * | 11/1998 | Marzynski et al. | 604/72 |
| 5,891,086 A | * | 4/1999 | Weston | 604/70 |
| 5,938,637 A | * | 8/1999 | Austin et al. | 604/72 |
| 6,096,002 A | * | 8/2000 | Landau | 604/68 |
| 6,309,371 B1 | * | 10/2001 | Deboer et al. | 604/68 |
| 6,572,581 B1 | * | 6/2003 | Landau | 604/68 |

(Continued)

FOREIGN PATENT DOCUMENTS

EP    1125593 A    8/2001

(Continued)

*Primary Examiner*—Sharon Kennedy
(74) *Attorney, Agent, or Firm*—The Culbertson Group, P.C.

(57) ABSTRACT

The invention relates to a needle-less injection device, comprising a cannula (5) which can be inserted in a housing (3), can be filled with a predetermined active substance (11) for injection, and comprises a piston (9) movable in a cannula housing for ejecting the active substance (11) from an outlet opening (53) in the cannula housing, and a propellant charge cartridge (7) insertable into the housing (3) and comprising a housing containing a propellant charge (19) and a device (23) for igniting the propellant charge, and a propelling surface (15) movable in a part (3a) of the housing of the injection device (1) or in the housing of the cannula (5) or in the cartridge housing and movable by the gas pressure, after ignition of the propellant charge (19), out of a starting position into an end position, the outer periphery of the propelling surface being sealed from the inner periphery of each housing during the entire displacement travel also, wherein the propelling surface (15) acts upon the piston (9) movable in the cannula housing.

33 Claims, 10 Drawing Sheets

U.S. PATENT DOCUMENTS 6,616,627 B1 * 9/2003 Willis et al. .................. 604/69
6,620,135 B1 * 9/2003 Weston et al. .............. 604/140

FOREIGN PATENT DOCUMENTS

| WO | WO 98/31409 | 7/1998 |
| WO | WO/99/21609 | 5/1999 |
| WO | WO 99/48546 | 9/1999 |
| WO | WO 00/29055 A | 5/2000 |

* cited by examiner

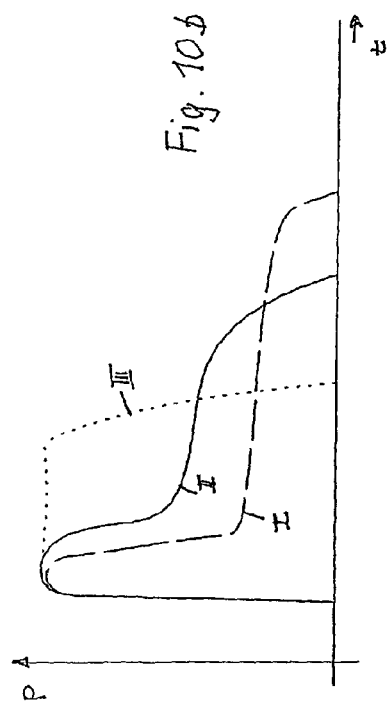
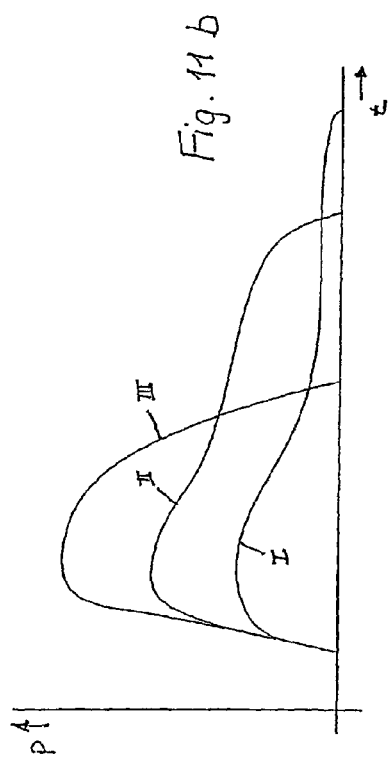
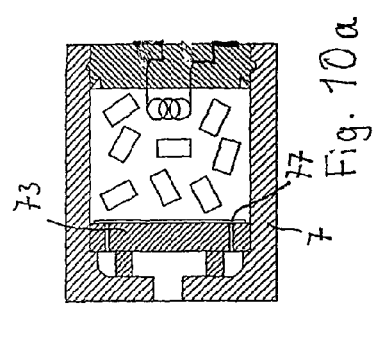
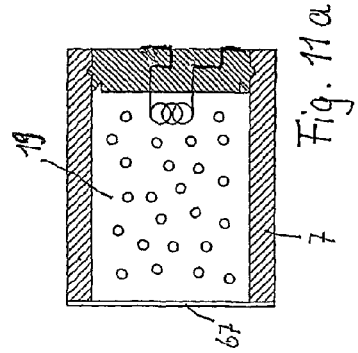
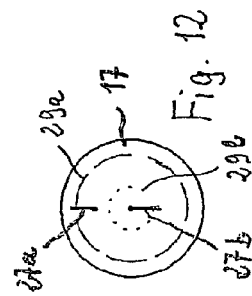

NEEDLELESS INJECTION DEVICE WITH PYROTECHNIC DRIVE

The invention relates to a needle-less injection device whereby an active substance can be injected at high pressure percutaneously or intramuscularly.

The basic principle of injecting an active substance by high pressure without using a needle, has long been known. U.S. Pat. No. 3,308,818 discloses an injection cartridge comprising a closed housing with a nozzle-like opening. A propellant charge is provided in the housing and can be activated by an ignition device. A spherical container holding the active substance for injecting is disposed between the propellant charge and the nozzle-like opening. The injection cartridge can be inserted in a revolver-like injection device comprising a mechanism for triggering the device for igniting the injection cartridge. After triggering of the ignition device, the propellant charge is activated, and the resulting gas pressure in the cartridge subjects the active-substance container to high pressure and squashes it. As a result, the container bursts in the neighborhood of the nozzle-like opening and the active substance for injection is delivered therefrom at high pressure.

WO 98/31409 discloses a needle-less injection system wherein the active substance for injection, in a disposable cartridge as before, is contained in a chamber, at least the major part of which is surrounded by a closed, sufficiently flexible and therefore compressible wall. The chamber as before has a nozzle-like opening which is closed in the initial state and can be opened before the injection, e.g. by breaking open a closure means. A propellant charge and an ignition device for activating it are provided in the rear region of the cartridge. When the propellant charge is activated, the resulting gas pressure drives the active substance in the chamber out of the nozzle-like opening.

Injection cartridges of this kind, however, have a disadvantage in that the active substance is contained beforehand in a flexible sheath in a closed chamber in the cartridge, and therefore a suitable cartridge must be produced for each dosage and each particular active substance. A doctor would therefore need to keep a large number of different cartridges in stock, at least for active substances frequently required in different doses. It may also be necessary to vary the propellant charge for different applications, e.g. different skin types or different required depth of penetration of the active substance, and so on. This further increases the number of different cartridges required.

Another disadvantage of these injection cartridges is that care always has to be taken that even after prolonged storage of the cartridges, the active substance is not disadvantageously influenced by the material constituting the wall enclosing it. A flexible wall of this kind can in practice be made only of plastic, e.g. PE, and consequently the materials used must be of suitable high quality, highly sealing-tight for a prolonged time, and consequently expensive. Also each type of cartridge must go through a lengthy approval procedure, since the cartridge as such is classed as a medicament and is therefore subject to strict licensing procedures.

Another disadvantage of these injection cartridges is the risk that the flexible sheath enclosing the active substance will be destroyed by the gas pressure produced by the propellant charge or by the particles produced by the gas. In such cases the active principle will be contaminated with the gas and the resulting particles. This may lead to inflammation or allergic reactions by the patients.

There are also known mechanical devices for needle-less injection, comprising a spring system which applies sufficient force to the piston of an injection cannula and moves the piston forward quickly enough for the active substance for injection to be discharged at high pressure from the outlet opening of the cannula. Such devices and cannulas are not subject to the strict regulations for licensing medicaments, owing to the use of disposable cannulas into which an active substance is drawn in conventional manner, just before the injection.

The disadvantages of purely mechanical needle-less injection systems are the expensive construction and expensive maintenance. Also, only a limited pressure for ejecting the active substance can be generated in the cannula. The nozzle-like outlet opening may therefore need to have a relatively large diameter, with the result that the injection will be more painful for the patient. Furthermore if the pressure is insufficiently high, the depth of penetration of the active substance may be inadequate. Finally spring-driven mechanical injection systems can accelerate the cannula piston only to a relatively small extent, so that the devices are unsuitable for applications in which a very rapid pressure increase is required.

U.S. Pat. No. 5,399,163 discloses a method of needle-less injection and a suitable device, wherein the piston of a cannula containing the active substance for injection can be acted upon by the pressure from a cartridge containing e.g. $CO_2$ gas. The device has a pressure-intensifying means in the form of springs and pistons. The construction is complicated, so the system is expensive. It also needs frequent maintenance, like all mechanical systems. Owing to its size and weight, the system is relatively difficult to handle. As in all mechanical systems, there is a limit to the rate at which the pressure for ejecting the active substance can be increased.

Starting from this prior art, the object of the invention is to devise a needle-less injection device which can be made easily and inexpensively, is easy to handle and is of universal use.

The invention solves this problem by the features in claim 1. The invention is based on the discovery that a pyrotechnic drive for actuating the piston of a cannula can if required produce an extremely steep increase in the pressure for ejecting the active substance from the cannula. Since a propellant charge cartridge is used, it can be exactly adapted to the required application. The required variation of pressure with time can be obtained by varying the propellant charge or the construction and dimensions of the propelling surface and the volume of the cartridge. For example the propellant charge can be a quick-acting powder in combination with a powder which acts more slowly but generates gas for a longer time. This is a means, e.g. of obtaining a very rapid pressure increase with a high peak followed by an initially constant and then slowly decreasing pressure curve. A propellant charge according to the invention means any material for generating an activatable gas.

The requirements on the cannula material are made less strict by providing a cannula which can be inserted into the injection-device housing and into which the active principle is introduced shortly before the injection.

Both the propelling surface and the cannula piston are disposed between the active substance for injection and the propellant charge or the gas generated by the propellant charge. Since both the propelling surface and the cannula piston are given a periphery which also remains sealed from the respective housing part during displacement, the risk of contaminating the active substance by the propellant charge gas or particles of the propellant charge is practically eliminated. The propellant charge can be held locked in its starting position in the respective housing. Means can also be provided for locking and holding the propelling surface in an end position.

This prevents the propelling surface from moving out of its starting position if the device moves, without being acted upon by the gas pressure from the propellant charge. The propelling surface is locked in the end position to prevent it falling out of the cartridge or remaining in the injection device when the cartridge is changed. It is always possible to see whether a cartridge constructed in this way has already been used, since the propelling surface cannot be accidentally moved back to its starting position.

Optionally in the preferred embodiment, the propelling surface, in the outer region of its end face acted upon by the gas pressure, has an annular recess such that when pressurized by the gas, the lid-like wall between the annular recess and the outer periphery of the propelling surface is pressed, with preferably elastic deformation, against the inner wall of the respective housing, so as to have a sealing effect. This simple feature avoids the need for an O-ring on the outer periphery of the propelling surface, so that production is simpler and cheaper.

In one embodiment, the propelling surface can be provided in a part of the housing of the injection device, the cartridge being a separate part and insertable into the said housing part. In this embodiment the propelling surface can be movable against the restoring force of a spring element, so that the propelling surface can be used more than once. In this case the propellant charge cartridge will not have a propelling surface of its own, but will simply produce gas. In an embodiment of this kind, however, traces of smoke will be left in the part of the housing in which the propelling surface is movably held, so that the said part is re-usable to only a limited extent. The part must frequently be cleaned and changed when necessary.

In this case the housing part can be in the form of a cartridge-like interchangeable part together with the propelling surface.

In another embodiment the propelling surface is provided in a cannula housing and the cartridge is a separate part insertable into the said housing.

Likewise the propelling surface can as before be disposed in the cannula housing, the cartridge being a separate part and insertable into the injection-device housing at the rear of the cannula.

In these cases also the cartridge can simply produce gas without a propelling surface of its own.

In another embodiment the cannula and the cartridge can form a single part, wherein the piston and the propelling surface will be disposed in the common cannula/cartridge housing. This embodiment is suitable e.g. for applications in which there is a very frequent requirement for the same cannula size with the same propellant charge.

In all cases in which the propelling surface is provided in the cannula housing or the common cannula/cartridge housing, the propelling surface can be integral with the piston or force-fit coupled thereto.

Optionally the axial distance between the means sealing the piston and the means sealing the propelling surface is greater than the distance traveled by the propelling surface between its starting position and its end position. The advantage of this is that the part of the inner wall of the housing co-operating with the means sealing the propelling surface need not be the same as the part co-operating with the means sealing the piston, in order to obtain a sealing effect. This results in improved reliability of operation as regards contamination of the active substance by the propelling gas or particles thereof.

In another exemplified embodiment of the invention, the cannula and the propellant charge cartridge can each be a separate part and insertable into the injection device. The propelling surface is provided in the propellant charge cartridge and preferably acts on the cannula piston as soon as inserted into the injection device. In this embodiment the propelling surface moves only inside the cartridge housing and is sealed therefrom. No smoke traces are therefore produced outside the cartridge housing (a propellant charge cartridge of this kind can also be used for other purposes than mechanical pyrotechnic drive devices).

After insertion into the injection device, the cannula (whether in the form of a separate part or a combined cannula/cartridge unit) can be supported by the injection-device housing over substantially its entire outer periphery. The cannula wall can therefore be made much thinner, since it does not have to withstand the full pressure.

According to the invention a propellant charge cartridge, with or without a propelling surface or a cannula/propellant charge cartridge unit, can have a companion chamber which in the starting position is connected to the housing chamber in which the gas is generated, or can be connected by movement of the propelling surface out of its starting position.

The companion chamber is a means of influencing the pressure increase and the subsequent variation in the compressive force exerted on the propelling surface.

Optionally the companion chamber is an annular chamber extending round the chamber in which gas is generated.

The annular chamber can be bounded by an end wall formed with one or more apertures which in the starting position are substantially sealed by the propelling surface. The end wall is formed with at least another, preferably concentric aperture, through which the gas generated by the propellant charge acts on the propelling surface.

The companion chamber of the annular chamber can be adjusted by an annular element engaging the rear end face of the annular chamber. The annular element can be moved e.g. by an adjusting mechanism, or different annular elements for insertion in the annular chamber can be provided for different applications.

The device for igniting the propellant charge cartridge or the cannula/propellant charge cartridge unit is preferably electrically actuated, in which case two connecting contacts of the ignition device extend from the rear end face of each respective housing so that their contact connecting surfaces lie in two imaginary non-overlapping concentric annular regions or in one imaginary concentric circle and one imaginary concentric annular region.

The device in the needle-less injection device for igniting the said propellant charge cartridge without a cannula/propellant charge cartridge unit can comprise two annular blade-like contacts or one concentric contact and one annular blade-like contact. This construction of the connecting contacts of the device for igniting the propellant charge cartridge or the cannula/propellant charge cartridge units, and the construction of the contacts of the ignition device, result in a reliable electric connection between the respective contacts after insertion of the propellant charge cartridge or cannula/propellant charge cartridge unit into the injection device, without the need to insert the cartridge in alignment.

The ignition device preferably comprises a battery movable against the restoring force of a spring element, wherein electric connecting leads are provided for connecting the battery terminals to the contacts of the ignition device if the battery is moved over at least a predetermined distance.

One terminal of the battery can abut an electrically conductive flexible diaphragm forming part of the respective electric connecting lead. The diaphragm is constructed so that it, if acted upon by a compressive force, enables the battery to move a sufficient distance.

This embodiment of the ignition device is simple and therefore inexpensive. Owing to the very simple mechanical construction, operation is very reliable. This embodiment, like the special design of the ignition-device contacts, can also be used for any other device.

Other exemplified embodiments of the invention are disclosed in the sub-claims.

The invention will now be explained in further detail with reference to exemplified embodiments shown in the drawings, in which.

FIG. 10 shows an embodiment of a propellant charge cartridge producing gas only (FIG. 10a) and a diagram showing possible variations in time of the pressure generated by the propellant charge cartridge (FIG. 10b), FIG. 11 comprises a drawing similar to FIG. 10, but with another embodiment of the propellant charge cartridge producing gas only, and FIG. 12 is a diagrammatic plan view of the rear of the propellant charge cartridges or cannula/propellant charge cartridge units according to the invention.

Figure 1:
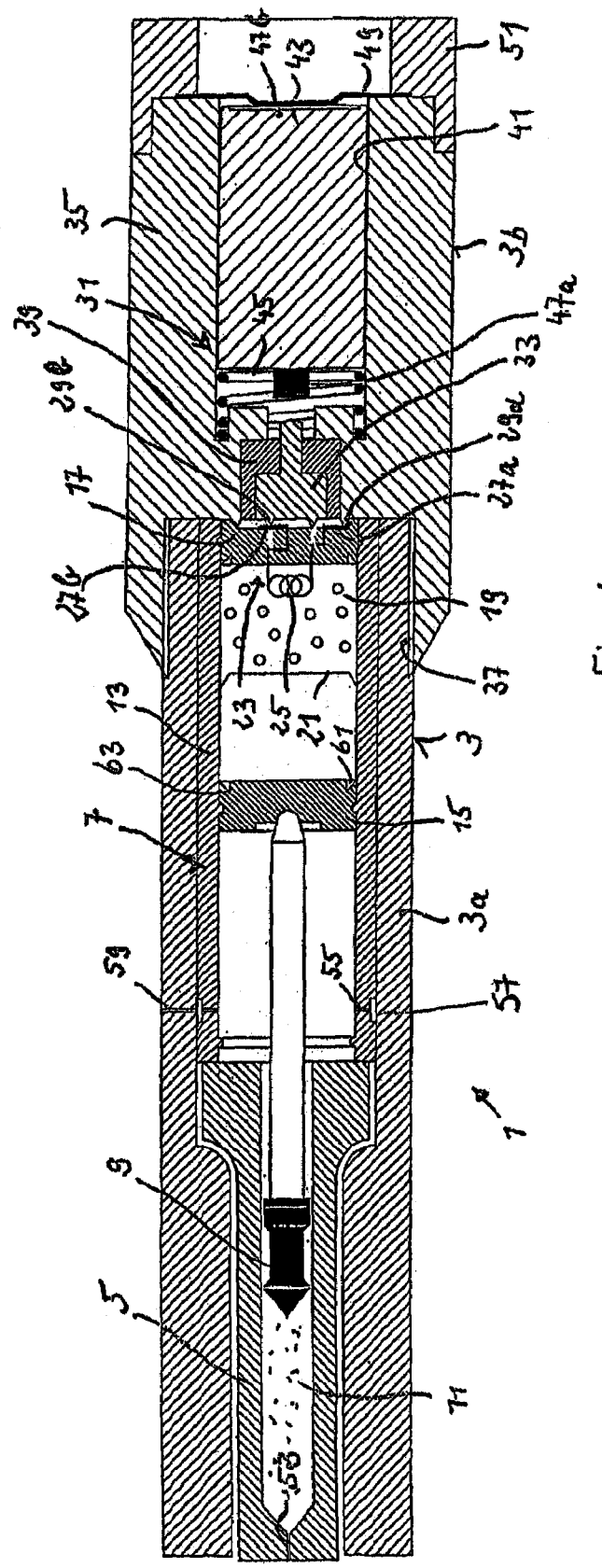
FIG. 1 is a longitudinal section through an injection device with a separate cannula and a separate propellant charge cartridge, wherein the propelling surface is provided in the propellant charge cartridge.

FIG. 1 shows an injection device 1 with a housing 3 comprising a front part 3a and a rear part 3b. The front part 3a holds a cannula 5 and a propellant charge cartridge 7. In the embodiment shown in FIG. 1, the region of the front housing part 3a which receives the cannula 5 and the propellant charge cartridge 7 is designed so that the cannula and the cartridge are insertable from the rear end of the housing part.

Alternatively of course the front housing part 3a may be constructed so that it can be swung up to insert the cannula and the propellant charge cartridge and then closed and locked.

In the embodiment shown the cannula 5 is substantially completely received in the housing part 3a and supported by the inner wall thereof. The outer contour of the cannula 5 is thus made complementary with the contour of the inner wall of the front region of the front housing part 3a. This feature enables the cannula walls to be made thinner, since the pressure exerted by the cannula piston 9 on the active substance in the front region of the cannula is absorbed by the wall of the front housing part 3a. In spite of the thin cannula walls and the high pressure in the front region of the cannula, the cannula walls cannot move outwards in the radial direction. There is thus a sealing effect between the outer wall of the piston and the inner wall of the cannula.

The rear region of the front housing part 3a holds the propellant charge cartridge 7, which has a preferably cylindrical wall 13 in the form of a tubular portion. A propelling surface 15 is provided in the cylindrical wall 13. The rear region of the cartridge 7 is tightly closed by a disc-like closure element 17. The cylindrical wall 13, the propelling surface 15 and the closure element 17 can all be made of plastic. The closure element 17 can be connected to the cylindrical wall 13 by locking. Preferably to this end the closure element 17 has an annular raised portion on its outer periphery, engaging in an annular groove on the inside of the cylindrical wall 13. Of course the closure element 17 can be connected to the wall 13 differently, e.g. by pinching, welding or the like.

A propellant charge 19 is provided in the rear region of the cartridge 7 preferably immediately in front of the closure element 17. The charge 19 preferably consists of a pyrotechnic material and is held in the rear region of the cartridge 7 by a retaining element 21, e.g. of cardboard.

An ignition device 23 in the rear region of the cartridge can e.g. comprise a spiral-wound filament 25 which extends into the region containing the propellant charge 19. The connecting contacts 27a, 27b of the ignition device 23 can extend from the rear end face of the closure element 17. As shown by a diagrammatic plan view of the closure element 17 in FIG. 12, the surfaces of the connecting contacts 27a, 27b of the ignition device 23 extend substantially radially on the end face of the closure element 17. The connecting contact 27b, disposed substantially centrally on the end face of the closure element 17, extends radially outwards from its central penetration point. The radially outer end of the connecting contact 27b ends in the radial direction in front of the imaginary circle through the penetration point of the connecting contact 27a. The connecting contacts 27a, 27b can thus be contacted by annular contacts 29a, 29b on an ignition device 31, which are preferably in the form of annular blade contacts. The lines of blade contacts 29a, 29b are shown in chain lines in FIG. 12.

The ignition device 31, which is disposed in the rear part 3b of the housing, comprises a first contact element 33 bearing the annular blade contact 29b. The contact element 33 is held in a front part 35 of the rear housing part 3b so that after the rear region of the front housing part 3a has been inserted into a receiving recess 37 in the front region of the front part 35, the blade contact 29b of the contact element 33 makes electric contact with the connecting contact 27b of the ignition device 23. The front part 35 of the rear housing part 3b can be connected to the front housing part 3a e.g. by screwing. The front part 35 of the rear part 3b is preferably of metal, so that the contact 29a in the recess 37 can be in the form of an annular raised portion on the bottom wall of the recess 37. In order electrically to insulate the contacts 29a and 29b, the contact element 33 is held by an insulating part 39 in the front part 35 of the rear housing part 3b. A recess 41 in the rear region of the part 35 holds a battery 43. In the recess 41, which extends axially, the battery is axially movable in the direction of the contact element 33 against the force of a spring 45. In the initial state the spring 45 breaks the electric contact between the contact element 33 and the front battery terminal 47a.

The rear battery terminal 47b is acted upon by an electrically conductive flexible or elastic diaphragm 49 which produces an electric contact between the terminal 47b and the part 35, either continuously or at least when the diaphragm is pressed against the rear terminal 47b. The diaphragm is preferably connected to the part 35 by a rear part 51 of the rear housing part 3b, and can be clamped between facing ends of the parts 35 and 51.

If the diaphragm 49 is subjected to a compressive force sufficient to push the battery 43 against the force of the spring 45 until the front terminal 47a is in contact with the contact element 33, the ignition device 23 will be activated. In the case shown in FIG. 1, the propellant charge 19 is ignited by the spiral-wound filament 25, which is heated by the current.

The resulting propelling gas acts on the propelling surface 15, which drives the piston 9, so that the active substance 11 is ejected from the nozzle-like outlet opening 53 at sufficiently high pressure, in the form of a strong jet.

As shown in FIG. 1, in the starting position shown in FIG. 1 the propelling surface 15 can be locked to the cylindrical wall 13 of the cartridge 7. This prevents accidental shifting of the propelling surface from its starting position. Locking occurs preferably by means of a raised portion formed on the inside of the wall 13 of the cartridge 7 and engaging in an annular groove in the outer periphery of the propelling surface. It is thus possible, when assembling the propellant charge cartridge 7, first to insert the propelling surface 15 from the rear end of the cartridge and to exert pressure on the propelling surface until it locks in the starting position. The closure element 17 and the wall 13 are locked in the reverse manner, for easy insertion of the propelling surface 15 during assembly.

A raised locking portion on the inside of the wall 13 can likewise be formed at the end position of the propelling surface 15 in the front region of the propellant charge cartridge 7. In this way the propelling surface is firmly secured in the end position and cannot fall out of the injection device 1 or remain in it when the cartridge 7 is taken out. In the embodiment shown in FIG. 1, the rear end of the cannula also serves as a stop for the propelling surface 15 in its end position. Alternatively of course a corresponding stop can be provided inside the wall 13 of the cartridge 7.

In its front region the cartridge 7 has one or more air outlet openings 55 which open into an annular groove 57 in the outer periphery of the cartridge 7. One or more air outlet openings 59 are also provided in the front housing part 3a and communicate with the annular groove 57. Air in front of the propelling surface during its forward motion can thus escape from the injection device, so that the propelling surface is not accidentally slowed down.

On its rear end face the propelling surface can have a peripheral recess 61 shaped so as to produce a lid-like annular part region 63 on the rear outer peripheral region of the propelling surface 15. When the propelling surface is acted upon by the propellant charge gas, the lid-like part region 63 is pressed against the inside of the wall 13 of the cartridge 7, resulting in a sealing effect.

Figure 2:
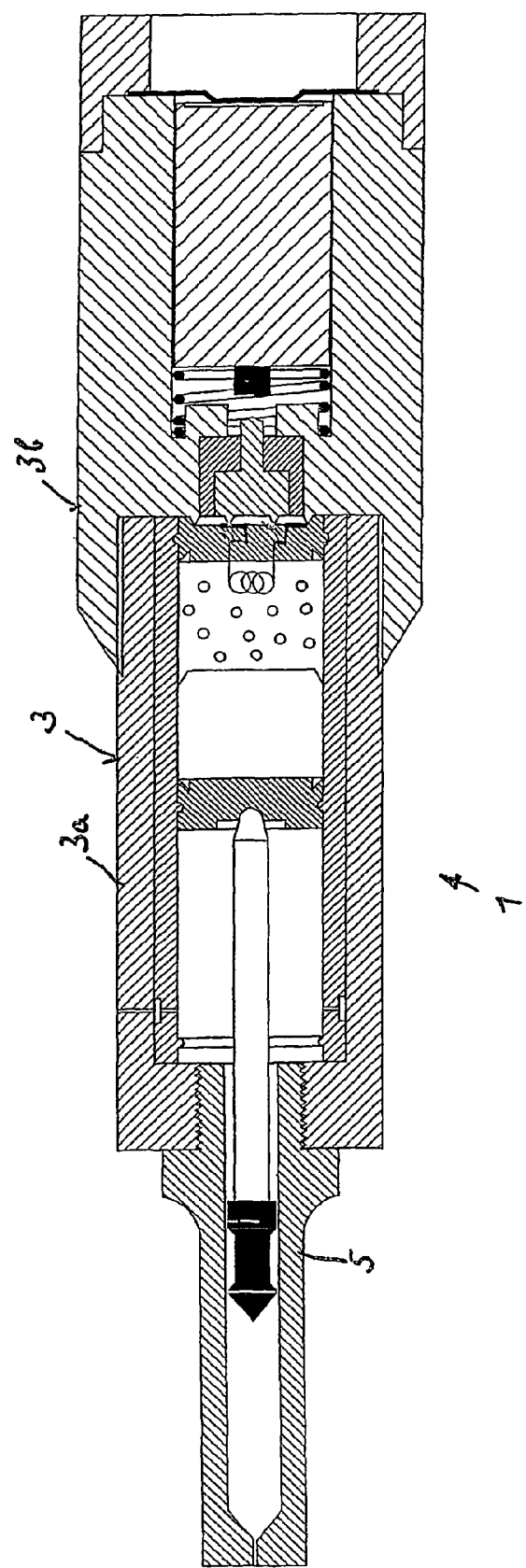
FIG. 2 is a longitudinal section through an injection device as in FIG. 1, comprising a cannula screwable into the injection device.
Figure 3:
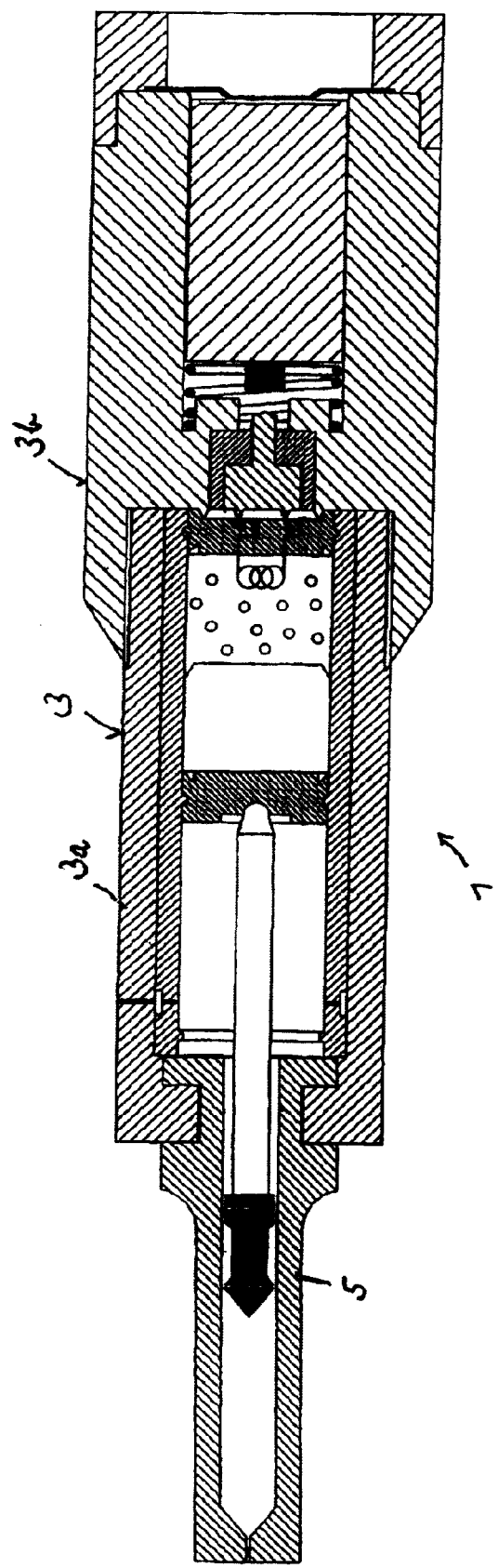
FIG. 3 is a longitudinal section through an injection device as in FIG. 1, comprising a cannula insertable into the injection device via a bayonet closure.

FIG. 2 shows an embodiment of an injection device 1 which differs from the embodiment in FIG. 1 in that the cannula 5 is screwable into a recess in the end face of the front housing part 3a. The cartridge wall must therefore be made thicker in this embodiment. In the embodiment shown in FIG. 3, the cannula 5 can be connected to the housing part 3a by a bayonet lock. The rear region of the cannula 5 and the receiving opening in the end face of the housing part 3a are shaped accordingly. In this embodiment also, the wall of the cannula 5 must be made thicker than in the embodiment in FIG. 1.

Figure 4:
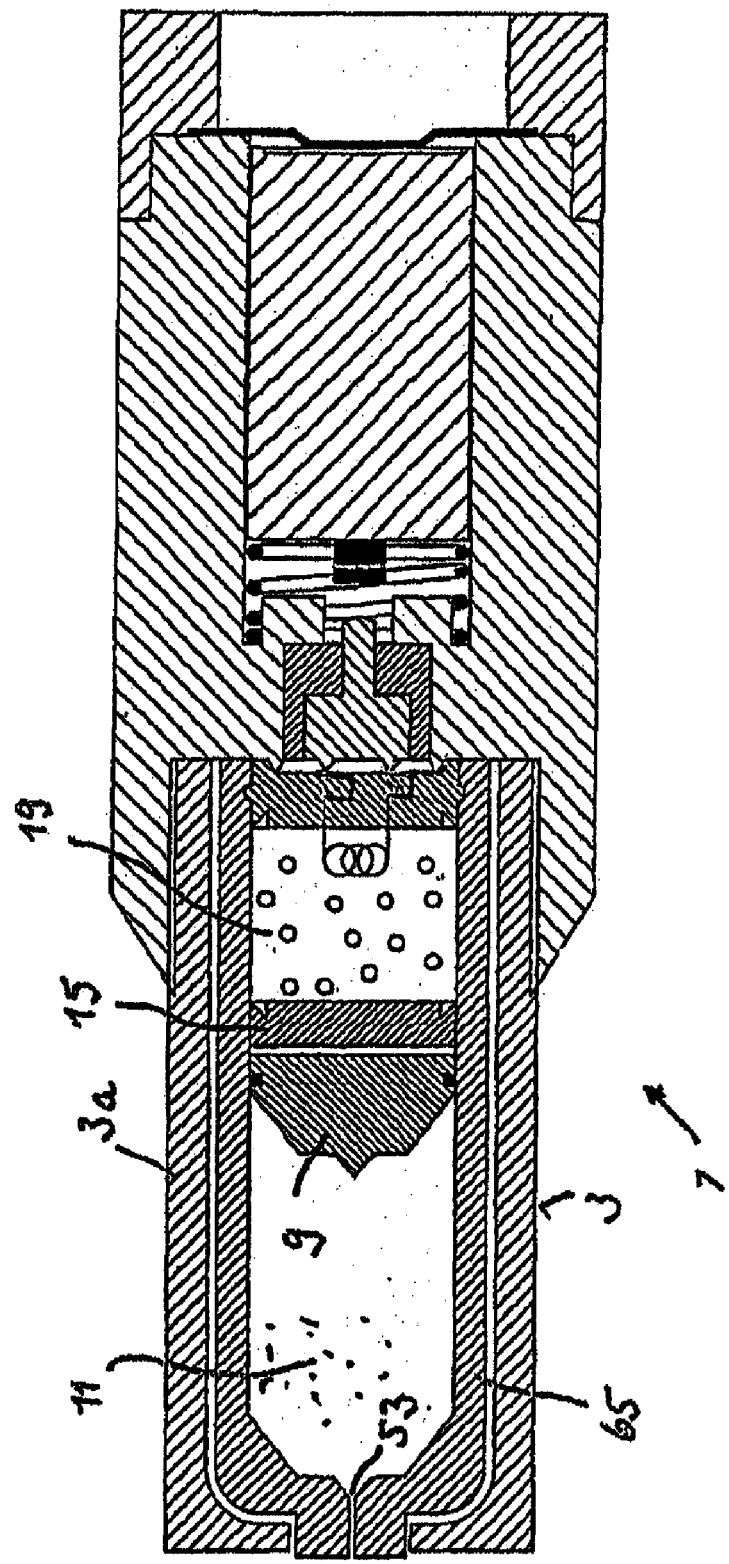
FIG. 4 is a longitudinal section through an injection device comprising a combined cannula/propellant charge cartridge unit.

FIG. 4 shows an embodiment of an injection device 1 in which the cannula and the propellant charge cartridge form an integrated cannula/propellant charge cartridge unit 65. A piston 9 is provided in the front cannula part of the cannula/propellant charge cartridge unit 65 and ejects the active substance 11 in front of the piston through the outlet opening 53. A propelling surface 15 is provided in the rear region of the cannula/propellant charge cartridge unit 65 and acts on the piston 9 and presses it forwards when the propellant charge 19 is ignited.

Figure 5:
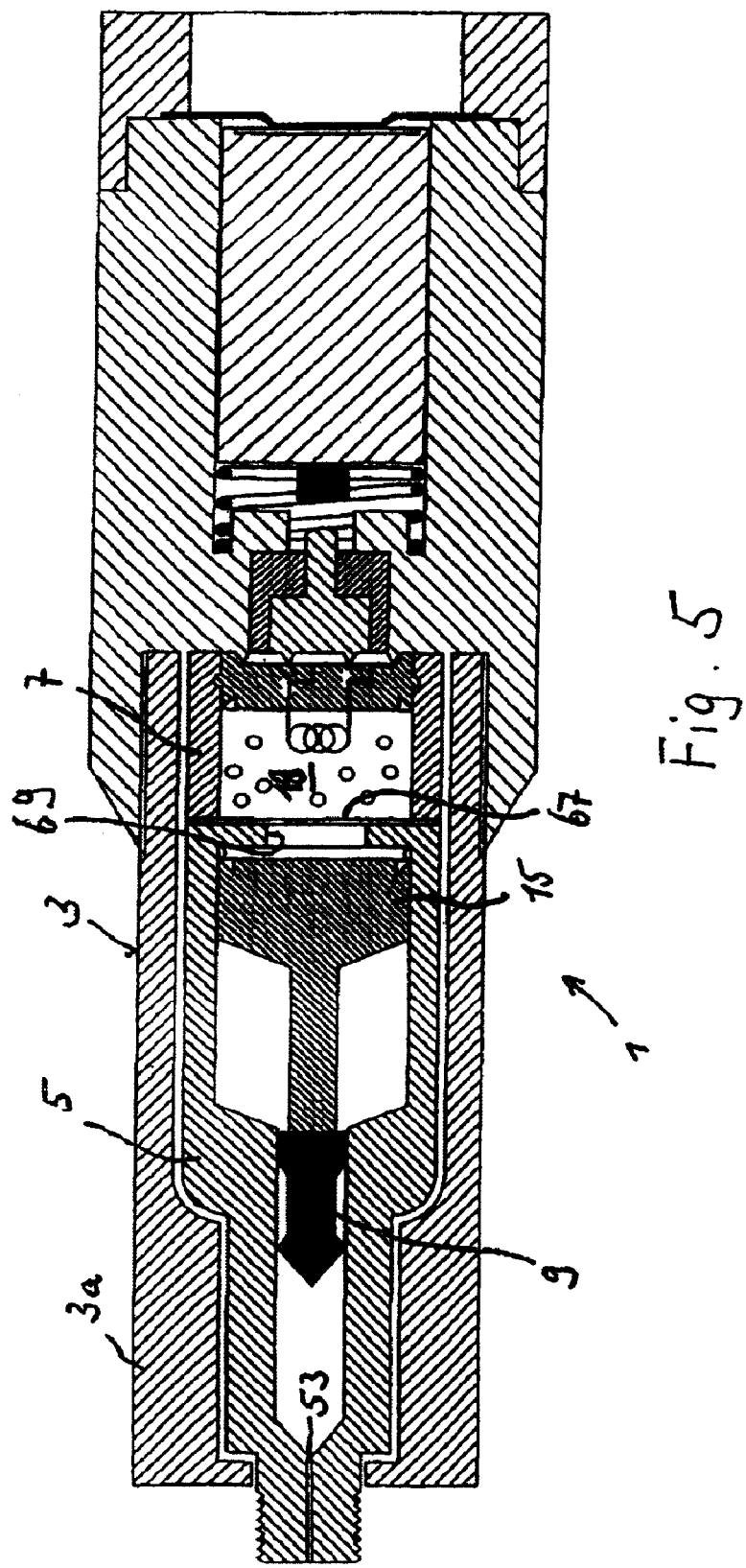
FIG. 5 is a longitudinal section through an injection device comprising a cannula containing a propelling surface coupled to the piston, and with a separate propellant charge cartridge without a propelling surface.

FIG. 5 shows an embodiment of an injection device 1 in which use is made of a cannula 5 containing a piston 9 rigidly connected to a propelling surface 15. As in the embodiments in FIGS. 1 and 4, the cannula 5 is received practically completely in the housing part 3a. A propellant charge cartridge 7 is received in the front housing part 3a in the rear region in the immediate neighborhood of the cannula 5, and is a gas-generating cartridge only. This embodiment of the cartridge 7 does not contain a propellant charge surface. The cartridge 7 in FIG. 5 has its front end face closed by a diaphragm 67. The diaphragm 67 holds the propellant charge 19 inside the cartridge 7 and also has a damming effect. If the propellant charge 19 is ignited, the diaphragm 67 seals the interior of the cartridge 7 until the gas pressure exceeds a predetermined threshold value and the diaphragm 67 breaks or bursts. The threshold pressure can be determined inter alia by the thickness of the diaphragm 67 and by additional bracing of the diaphragm if required.

As shown in FIG. 5, the cannula 5 at its rear end can have an aperture 69, so that the diaphragm 67 is supported by the remaining regions of the rear end wall of the cannula 5. Depending on the diameter of the aperture 69, the diaphragm 67 will burst at a higher threshold pressure (at smaller diameters of the aperture 69) or at lower threshold pressures (at greater diameters of the aperture 69).

The advantage of the cannula 5 constructed as in FIG. 5 is that the piston and the propelling surface are each guided in individual regions of the cannula housing. This improves the reliability in operation, since the seal on the two elements is not broken if the inner wall of the cannula 5 is damaged.

Instead of a rigid connection, of course, the piston 9 and the propelling surface 15 can be force-fit connected. The advantage of this is that the propelling surface 15 can remain in its starting position and the piston 9 can be provided in its starting position in the front region of the cannula. Only when the cannula is filled with the active substance through the outlet opening 53, is the piston 9 retracted to the maximum extent until its rear end comes against the front of the propelling surface 15.

Figure 6:
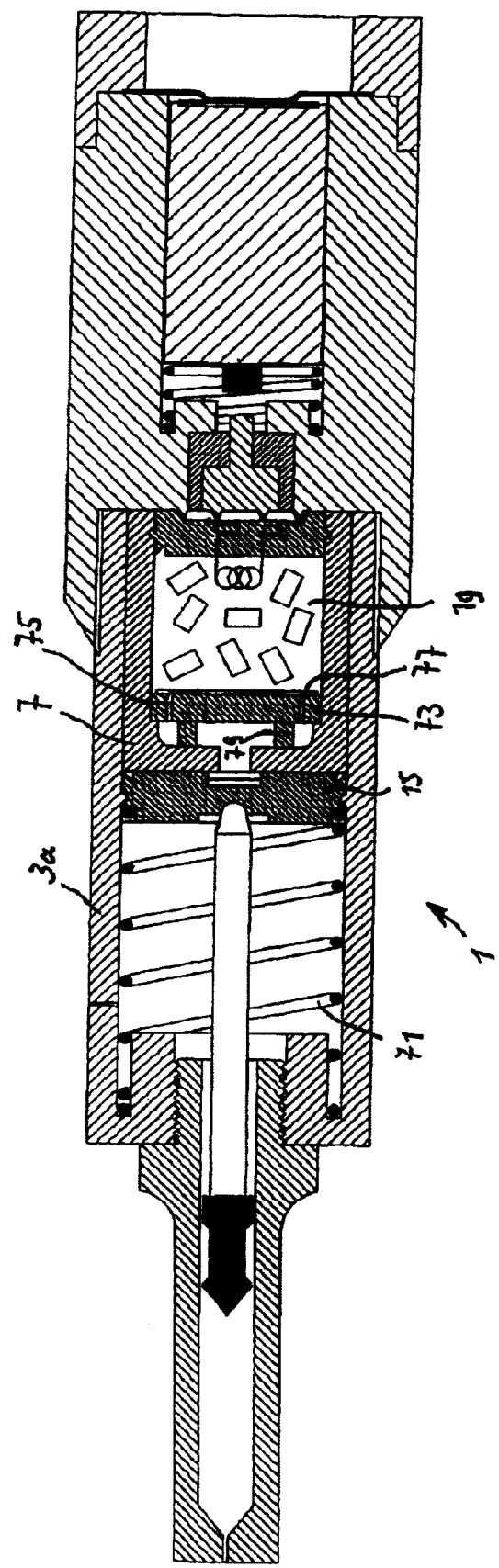
FIG. 6 is a longitudinal section through an injection device with a re-usable housing part in which a propelling surface is provided and into which a propellant charge cartridge can be inserted.

FIG. 6 shows an injection device 1 comprising a front housing part 3a in which a propelling surface 15 is movable against the force of a spring 71. The rear region of the part 3a holds a cartridge 7, which as before generates gas only.

In this embodiment of an injection device the housing part 3a is in the form of an interchangeable cartridge, since traces of smoke are produced when the propellant charge 19 is ignited inside the part 3a. In this case the part 3a and the surface 15 are re-usable but the interior 3a needs frequent cleaning and the cartridge in the form of the housing part 3a must be replaced after being used a predetermined maximum number of times.

The propellant charge cartridge 7 differs from the cartridge (likewise gas-producing only) in the device in FIG. 5, in that a wall 73 is provided in the front region of the cartridge and has a number of small-section apertures 75. On the inner side of the wall 73, the apertures 75 are closed by a diaphragm 77. On its front surface the wall 73 has a number of supporting feet 79 which bear against an end wall of the propellant charge cartridge 7. The supporting feet 79 ensure that the apertures 75 are not tightly closed by the end wall of the cartridge 7 (in conjunction with the end wall of the cartridge 7), so that the wall 73 is not broken or ejected from the propellant charge cartridge 7.

Owing to the small cross-section of the apertures 75, the propellant charge can react relatively slowly after ignition (i.e. produce a slower pressure increase). Owing to the damming effect of the wall 73 and the diaphragm 77, a very high threshold pressure has to be overcome before gas is expelled from the cartridge 7, when the diaphragm 77 breaks. The advantage however of using a slow-reacting propellant charge is that the gas pressure is kept constant over a prolonged period or falls more slowly than in the case of a rapidly reacting propellant charge powder as used in the embodiments in FIGS. 1 to 5.

In the embodiments in FIGS. 1 to 5, in order to generate a rapid pressure increase in the region in front of the piston 9 owing to the absence of substantial damming, it is necessary to use a propellant charge containing at least one quick-reacting component. Otherwise in this embodiment, the surface 15 and consequently the piston 9 would be accelerated relatively slowly owing to the slow increase in the pressure of the propellant charge gas.

Alternatively of course a slow-reacting propellant charge can be used in the embodiments in FIGS. 1 to 5 also, if similar use is made of a damming means such as the wall 73 and diaphragm 77 in FIG. 6.

It should be noted at this stage that a propellant charge comprising a slow-reacting component and a quick-reacting component may also be used in all embodiments. The mixing ratio and the form of damming (if necessary) must be chosen so that the gas pressure acting on the propelling surface varies as required.

Figure 7:
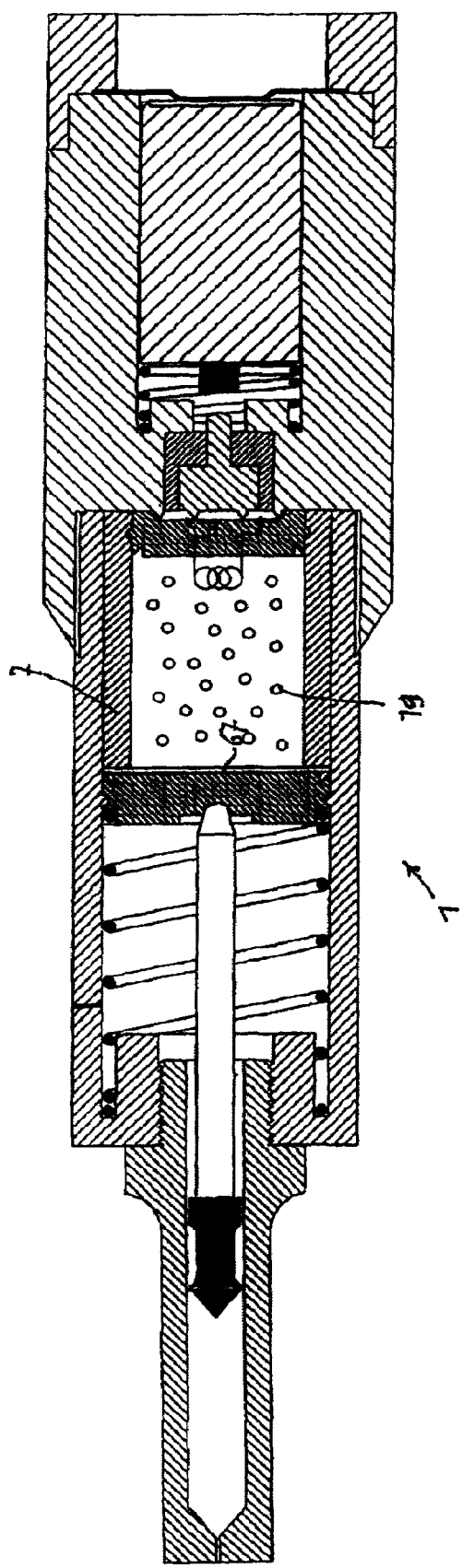
FIG. 7 is a longitudinal section through an injection device as in FIG. 6, but with a modified propellant charge cartridge.

FIG. 7 shows an embodiment of an injection device 1 which substantially corresponds to the embodiment in FIG. 6, except that in the present case a propellant charge cartridge 7 with a quick-reacting propellant charge 19 is again used. This is necessary, since the propellant charge cartridge 7 in its front region is used only with a diaphragm 67 (corresponding to the diaphragm of the propellant charge cartridge in FIG. 5). There is thus no substantial damming effect.

Figure 8:
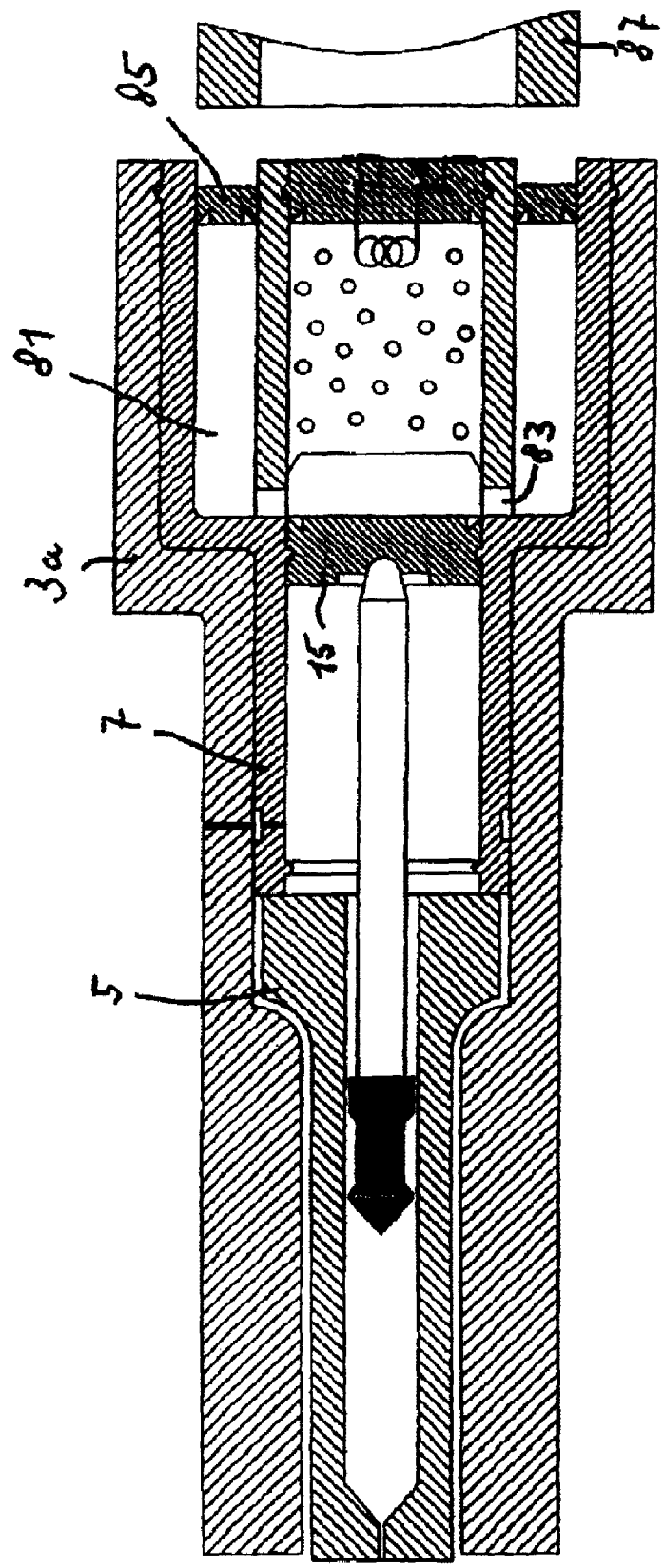
FIG. 8 is a longitudinal section through the front region of an injection device with a separate cannula and a separate propellant charge cartridge, a companion chamber being formed in the propellant charge cartridge.

FIG. 8 shows another embodiment of an injection device 1, largely similar to the embodiment in FIG. 1. The propellant charge cartridge 7, however, also has a companion chamber 81 which surrounds the space in which the propellant charge gas is generated. The annular chamber 81 is connected through apertures 83 to the space in which the propelling gas is generated. The companion chamber can produce a larger volume of propelling gas until the propelling surface 15, which also has a slight damming effect, is moved out of its starting position. When the surface 15 moves forward, the pressure of the propellant charge gas decreases more slowly owing to the greater volume generated before the propelling surface moves.

The companion chamber 81 is sealed by an annular sealing element 85. The element 85 can be moved in the annular chamber by an adjusting ring 87, shown only diagrammatically in FIG. 8. The ring 87 can either be permanently connected to the rear housing part 3b, which is connectable to the housing part 3a, or can be an independent part inserted between the sealing element 85 and the rear housing part 3b.

Different adjusting rings 87 having different axial dimensions, can be used for different applications requiring different sizes of companion chamber 81. Alternatively of course an adjusting ring 87 axially movable by an adjusting mechanism can be provided in the housing part 3b.

As described previously in connection with the propelling surface, the element 85 can be sealed by forming two peripheral recesses on the end face pressurized by the gas, each recess defining a sealing-tight lid-like region.

Figure 9:
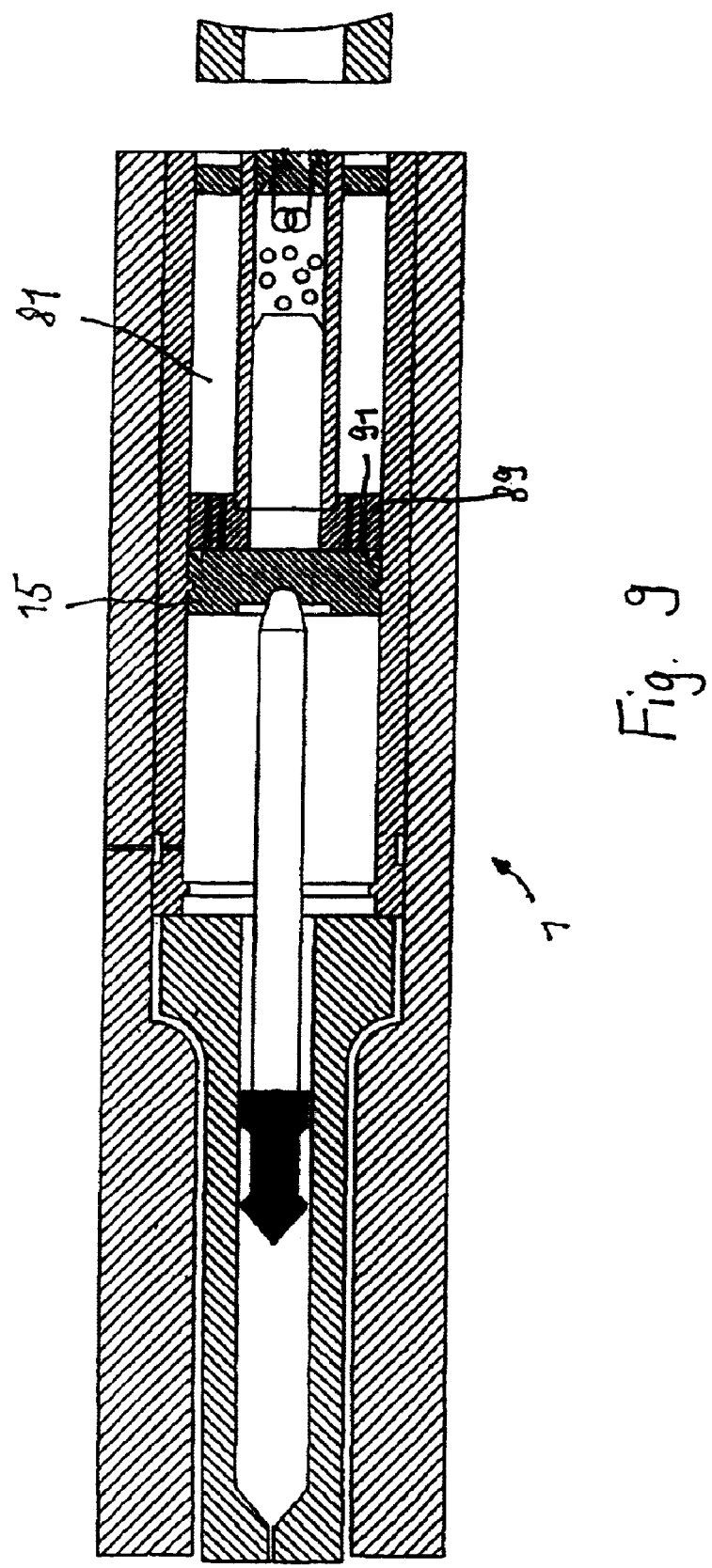
FIG. 9 is a longitudinal section through the front region of an injection device similar to FIG. 8, with a modified propellant charge cartridge.

FIG. 9 shows an embodiment of an injection device 1 which also has a companion chamber 81 extending in a ring around the space in which the propellant charge gas is generated. In this embodiment a wall 89 formed with a number of apertures 91 is provided between the propelling surface and the annular chamber 81.

In its starting position, the rear surface of the propelling surface 15 acts on the front end surface of the wall 89 and seals the apertures 91. In the starting position, therefore, the companion chamber 81 is not connected to the space in which the propelling gas is generated. A connection between the chamber 81 and the chamber in which the propelling gas is generated is made only after the propelling surface 15 moves out of its starting position. The resulting gas pressure acting on the propelling surface is at a peak when the surface 15 moves out of its starting position and then falls to a lower value, but this value is maintained longer than would be the case without a companion chamber.

FIGS. 10 and 11 once again show what type of propellant charge cartridge can be used to obtain what curve of the gas pressure P acting on the propelling surface.

FIG. 10a shows a propellant charge cartridge 7 which generates gas only, as previously described in connection with FIG. 6. Owing to the use of a relatively slow-reacting propellant charge (indicated by roughly-drawn "grains" or "pellets" of propellant charge powder) and the damming by the wall 73 and the diaphragm 77, before the diaphragm 77 bursts a high pressure builds up and falls relatively quickly to a lower value when the propelling surface acted upon by the gas moves out of its starting position in which the chamber volume of the cartridge 7 was relatively small. The lower value, however, can be kept for a longer time than would be possible with an exclusively quick-acting propellant charge. The various curves of pressure with time shown in FIG. 10b can be obtained with different propellant charges. Curve I can be produced e.g. with a relatively quick-acting propellant charge. Curve II is obtainable with a slower-acting propellant charge and curve III with a very slow-acting propellant charge or with a quick-acting propellant charge in combination with a slow-acting charge.

Owing to the damming in the embodiment of the propellant charge cartridge 7 in FIG. 10a, all three curves I, II, III have the same maximum pressure at which the diaphragm 77 bursts.

In the embodiment of a propellant charge cartridge 7 which generates gas only, as already described in connection with the embodiment of an injection device in FIG. 7, there is no appreciable damming effect. The main purpose of the diaphragm 67 is only to hold the propellant charge 11 in the interior of cartridge 7. The result, in the case of a slow-acting propellant charge, is the pressure curve I in FIG. 11*b*. The diaphragm 67 bursts at a relatively low maximum pressure, which then falls to a lower pressure which can be held for a relatively long time.

A quicker-reacting propellant charge results in the curve II in FIG. 11*b*. As before the diaphragm 67 bursts at a threshold pressure below the maximum pressure. The maximum pressure is mainly dependent only on the rate of increase in volume of the gas generated. The result is a higher maximum pressure than in curve I, a shorter time during which the pressure can be kept approximately constant or slowly decreases, and another region in which the pressure quickly falls to zero.

A quick-acting propellant charge results in a very high maximum pressure and practically no region in which the pressure can be held approximately constant for a prolonged period, so that the curve III falls relatively quickly from maximum pressure to zero.

Finally it should be pointed out that the features of the injection device, the cannula, the propellant charge cartridge and the ignition device described in connection with particular embodiments can be applied similarly to other embodiments. The exemplified embodiments of the propellant charge cartridges shown and/or described can if required be used for purposes other than for a needle-less injection device.

The invention claimed is:

1. A needle-less injection device, comprising
   (a) a cannula (5) insertable in a housing (3), and fillable with a predetermined active substance (11) for injection, and comprises a piston (9) movable in a cannula housing for ejecting the active substance (11) from an outlet opening (53) in the cannula housing,
   (b) a propellant charge cartridge (7) insertable into the housing (3) and comprising a housing containing a propellant charge (19) and a device (23) for igniting the propellant charge (19),
   (c) a propelling surface (15) movable in a part (3*a*) of the housing of the injection device (1) or in the housing of the cannula (5) or in the cartridge housing and movable by the gas pressure generated after ignition of the propellant charge (19), out of a starting position into an end position, the outer periphery of the propelling surface being sealed from the inner periphery of each housing during the entire displacement, wherein the propelling surface (15) acts upon the piston (9) movable in the cannula housing, and
   (d) wherein the propelling surface (15), in the outer region of its end face acted upon by the gas pressure, has an annular recess such that when pressurized by the gas, a lid-like wall (63) between the annular recess and the outer periphery of the propelling surface (15) is pressed, with preferably elastic deformation, against the inner wall of the respective housing, so as to have a sealing effect.

2. The injection device according to claim 1, wherein the propelling surface (15) is held locked in the starting position in the respective housing.

3. The injection device according to claim 1, wherein positioning means are provided in each housing for locking and holding the propelling surface (15) in the end position.

4. The injection device according to claim 1, wherein the propelling surface (15) is provided in the part (3*a*) of the housing of the injection device (1) and the propellant charge cartridge (7) is a separate part and is insertable into the housing part (3*a*).

5. The injection device according to claim 4, wherein the propelling surface (15) is movable by the gas pressure against the restoring force of a resilient element (71).

6. The injection device according to claim 4, wherein the housing part (3*a*) is a cartridge-like interchangeable part.

7. The injection device according to claim 1, wherein the propelling surface (15) is provided in the cannula housing and the propellant charge cartridge (7) is a separate part and insertable into the cannula housing.

8. The injection device according to claim 7, wherein the propelling surface (15) is integral with the piston (9) or is force-fit coupled thereto.

9. The injection device according to claim 8, wherein the axial distance between the means sealing the piston (9) and the means sealing the propelling surface (15) is greater than the distance traveled by the propelling surface (15) between the starting position and the end position.

10. The injection device according to claim 1, wherein the propelling surface (15) is provided in the cannula housing and the propellant charge cartridge (7) is a separate part insertable into the housing (3) of the injection device (1) at the rear end of the cannula (5).

11. The injection device according to claim 1, wherein the cannula (5) and the propellant charge cartridge (7) form a unit (65), wherein the piston (9) and the propelling surface (15) are provided in the common cannula/cartridge housing.

12. The injection device according to claim 1, wherein the cannula (5) and the propellant charge cartridge (7) are separate parts, and the propelling surface (15) is provided in the cartridge housing and is positive-fit or force-fit coupled to the piston (9).

13. The injection device according to claim 1, wherein a rear region of the cannula (5) is insertable into the housing of the injection device (1) or into the part (3*a*) thereof in which the propelling surface (15) is disposed, by screwing or by means of a bayonet closure.

14. The injection device according to claim 1, wherein the cannula (5) is supported substantially over its entire outer periphery by the housing (3) of the injection device (1).

15. The injection device according to claim 14, wherein the cannula (5) comprises a bearing surface which co-operates with a substantially complementary abutment surface on the housing (3), the cannula (5) on actuation of the piston (9) of the cannula (5) for ejecting the active substance (11) for supporting the cannula (5) in the axial direction.

16. A cannula/propellant charge cartridge unit for a device for needle-less injection comprising
   (a) a cannula/cartridge housing, an activatable propellant charge (19) provided therein, and an ignition device (23) for activating the propellant charge (19);
   (b) a piston (9) movable in sealing-tight manner in the cannula/cartridge housing for ejecting an active substance (11) from an outlet opening (53) in the cannula/cartridge housing;
   (c) a propelling surface (15) disposed in the cannula/cartridge housing, sealed from the inner wall of the housing, and movable by the gas pressure generated after ignition of the propellant charge (19) so as to drive the piston (9) out of a starting position into an end position, the outer periphery of the propelling surface

(15) being sealed against the inner periphery of the cannula/cartridge housing during the entire displacement; and (d) wherein the housing has a companion chamber (81) which is in fluid communication with the housing chamber in which the gas is generated when the propelling surface (15) is in the starting position, or is in fluid communication with the housing chamber in which gas is generated by movement of the propelling surface (15) out of the starting position.

17. The cannula/propellant charge cartridge unit according to claim 16 wherein a stop defining the end position of the propelling surface (15) is provided in the cannula/cartridge housing.

18. The cannula/propellant charge cartridge unit according to claim 16 wherein the propelling surface (15) is integral with the piston (9) or is force-fit coupled thereto.

19. The cannula/propellant charge cartridge unit according to claim 18, wherein the axial distance between the means sealing the piston (9) and the means sealing the propelling surface (15) is greater than the distance traveled by the propelling surface (15) between the starting position and the end position.

20. The cannula/propellant charge cartridge unit according to claim 16, wherein the companion chamber (81) is an annular chamber which extends around the chamber in which the gas is generated.

21. The cannula/propellant charge cartridge unit according to claim 20, wherein the annular chamber is bounded by an end wall (89) formed with one or more apertures (91) which are substantially sealed by the propelling surface (15) in the starting position, and the end wall (89) is formed with at least one aperture (91) through which the gas generated by the propellant charge (19) acts on the propelling surface (15).

22. The cannula/propellant charge cartridge unit according to claim 20, wherein the companion chamber (18) of the annular chamber is adjustable by an annular element engaging the rear end face of the annular chamber.

23. A propellant charge cartridge for a needle-less injection device comprising (a) a cartridge housing, a propellant charge (19) activatable therein, and an ignition device (23) for activating the propellant charge (19), (b) a propelling surface (15) disposed in the cartridge housing and sealed against the inner wall thereof, wherein the propelling surface (15) being movable by the gas pressure generated after ignition of the propellant charge (19) so as to drive the piston (9) of the cannula (5) containing an active substance (11) for injecting out of a starting position into an end position, the outer periphery of the propelling surface (15) being sealed from the inner periphery of the cartridge housing during the entire displacement, and (c) wherein the housing has a companion chamber (81) which is in fluid communication with the housing chamber in which the gas is generated when the propelling surface (15) is m the starting position, or is in fluid communication with the housing chamber in which the gas is generated by movement of the propelling surface (15) out of the starting position.

24. The propellant charge cartridge according to claim 23, wherein the companion chamber (81) is an annular chamber which extends around the chamber in which the gas is generated.

25. The propellant charge cartridge according to claim 24, wherein the annular chamber is bounded by an end wall (89) formed with one or more apertures (91) which are substantially sealed by the propelling surface (15) in the starting position, and the end wall (89) is formed with at least one aperture (91) through which the gas generated by the propellant charge (19) acts on the propelling surface (15).

26. The propellant charge cartridge according to claim 24, wherein the companion chamber (18) of the annular chamber is adjustable by an annular element engaging the rear end face of the annular chamber.

27. A propellant charge cartridge for a needle-less injection device comprising (a) a cartridge housing, a propellant charge (19) activatable therein, and an ignition device (23) for activating the propellant charge (19), (b) a propelling surface (15) disposed in the cartridge housing and sealed against the inner wall thereof, wherein the propelling surface (15) being movable by the gas pressure generated after ignition of the propellant charge (19) so as to drive the piston (9) of the cannula (5) containing an active substance (11) for injecting out of a starting position into an end position, the outer periphery of the propelling surface (15) being sealed from the inner periphery of the cartridge housing during the entire displacement, and (c) wherein the propelling surface (15) in the cartridge housing is held locked in the starting position, wherein locking projections are provided on the inner wall of the cartridge housing and co-operate with the peripheral edges of the propelling surface (15) or with one or more locking recesses in its peripheral surface.

28. A propellant charge cartridge for a needle-less injection device comprising (a) a cartridge housing, a propellant charge (19) activatable therein, and an ignition device (23) for activating the propellant charge (19), (b) a propelling surface (15) disposed in the cartridge housing and sealed against the inner wall thereof, wherein the propelling surface (15) being movable by the gas pressure generated after ignition of the propellant charge (19) so as to drive the piston (9) of the cannula (5) containing an active substance (11) for injecting out of a starting position into an end position, the outer periphery of the propelling surface (15) being sealed from the inner periphery of the cartridge housing during the entire displacement, and (c) wherein the positioning means for locking and holding the propelling surface (15) in the end position are provided in the cartridge housing, and the corresponding locking projections are provided on the inner wall of the cartridge housing and co-operate with the peripheral edges of the propelling surface (15) or with one or more locking recesses in the peripheral surface thereof.

29. A propellant charge cartridge for a needle-less injection device comprising (a) a cartridge housing, a propellant charge (19) activatable therein, and an ignition device (23) for activating the propellant charge (19), (b) a propelling surface (15) disposed in the cartridge housing and sealed against the inner wall thereof, wherein the propelling surface (15) being movable by the gas pressure generated after ignition of the propellant charge (19) so as to drive the piston (9) of the cannula (5) containing an active substance (11) for injecting out of a starting position into an end position, the outer periphery of the propelling surface (15) being sealed from the inner periphery of the cartridge housing during the entire displacement, and (c) wherein the propelling surface (15), in the outer region of its end face acted upon by the gas pressure, has an annular recess such that when pressurized by the gas, a lid-like wall (63) between the annular recess and the outer periphery of the propelling surface (15) is pressed against the inner wall of the respective housing, so as to have a sealing effect.

30. A cannula/propellant charge cartridge unit for a device for needle-less injection comprising
   (a) a cannula/cartridge housing, an activatable propellant charge (19) provided therein, and an ignition device (23) for activating the propellant charge (19);
   (b) a piston (9) movable in a sealing-tight manner in the cannula/cartridge housing for ejecting an active substance (11) from an outlet opening (53) in the cannula/cartridge housing;
   (c) a propelling surface (15) disposed in the cannula/cartridge housing, sealed from the inner wall of the housing, and movable by the gas pressure generated after ignition of the propellant charge (19) so as to drive the piston (9) out of a starting position into an end position, the outer periphery of the propelling surface (15) being sealed against the inner periphery of the cannula/cartridge housing during the entire displacement; and
   (d) wherein the propelling surface (15) in the cannula/cartridge housing is held locked in the starting position, and locking projections are preferably provided on the inner wall of the cannula/cartridge housing and co-operate with the peripheral edges of the propelling surface (15) or with one or more locking recesses in its peripheral surface.

31. A cannula/propellant charge cartridge unit for a device for needle-less injection comprising
   (a) a cannula/cartridge housing, an activatable propellant charge (19) provided therein, and an ignition device (23) for activating the propellant charge (19);
   (b) a piston (9) movable in a sealing-tight manner in the cannula/cartridge housing for ejecting an active substance (11) from an outlet opening (53) in the cannula/cartridge housing;
   (c) a propelling surface (15) disposed in the cannula/cartridge housing, sealed from the inner wall of the housing, and movable by the gas pressure generated after ignition of the propellant charge (19) so as to drive the piston (9) out of a starting position into an end position, the outer periphery of the propelling surface (15) being sealed against the inner periphery of the cannula/cartridge housing during the entire displacement; and
   (d) wherein the propelling surface (15), in the outer region of its end face acted upon by the gas pressure, comprises an annular recess such that when pressurized by the gas, a lid-like wall (63) between the annular recess and the outer periphery of the propelling surface (15) is pressed, with elastic deformation, against the inner wall of the cannula/cartridge housing, so as to have a sealing effect.

32. A propellant charge cartridge for a needle-less injection device comprising
   (a) a cartridge housing, a propellant charge (19) activatable therein, and an ignition device (23) for activating the propellant charge (19),
   (b) a propelling surface (15) disposed in the cartridge housing and sealed against the inner wall thereof, wherein the propelling surface (15) being movable by the gas pressure generated after ignition of the propellant charge (19) so as to drive the piston (9) of the cannula (5) containing an active substance (11) for injecting out of a starting position into an end position, the outer periphery of the propelling surface (15) being sealed from the inner periphery of the cartridge housing during the entire displacement, and
   (c) wherein the ignition device (23) is electrically actuated and two connecting contacts (27a, 27b) extend from the rear end face of the cartridge housing so that their surfaces lie in two imaginary concentric annular regions or in one imaginary concentric circle and one imaginary concentric annular region.

33. A cannula/propellant charge cartridge unit for a device for needle-less injection comprising
   (a) a cannula/cartridge housing, an activatable propellant charge (19) provided therein, and an ignition device (23) for activating the propellant charge (19);
   (b) a piston (9) movable in a sealing-tight manner in the cannula/cartridge housing for ejecting an active substance (11) from an outlet opening (53) in the cannula/cartridge housing;
   (c) a propelling surface (15) disposed in the cannula/cartridge housing, sealed from the inner wall of the housing, and movable by the gas pressure generated after ignition of the propellant charge (19) so as to drive the piston (9) out of a starting position into an end position, the outer periphery of the propelling surface (15) being sealed against the inner periphery of the cannula/cartridge housing during the entire displacement; and
   (d) wherein the ignition device (23) is electrically actuated and two connecting contacts (27a, 27b) extend from the rear end face of the cannula/cartridge housing so that their surfaces lie in two imaginary concentric annular regions or in one imaginary concentric circle and one imaginary concentric annular region.

* * * * *

UNITED STATES PATENT AND TRADEMARK OFFICE
CERTIFICATE OF CORRECTION

PATENT NO. : 7,160,265 B2
APPLICATION NO. : 10/311200
DATED : January 9, 2007
INVENTOR(S) : Peter Lell It is certified that error appears in the above-identified patent and that said Letters Patent is hereby corrected as shown below:

At column 13, line 58:
Change "surface (15) is m the" to --surface (15) is in the--.

Signed and Sealed this

Tenth Day of April, 2007

JON W. DUDAS
*Director of the United States Patent and Trademark Office*